United States Patent
Imamura et al.

(10) Patent No.: US 6,287,771 B1
(45) Date of Patent: Sep. 11, 2001

(54) METHOD FOR DETERMINING MASTITIS USING KERATIN AND CASEIN WHICH ARE AMPLIFIED BY PRIMERS

(75) Inventors: Mio Imamura; Yasuharu Itagaki; Morimasa Tanimoto, all of Hokkaido (JP)

(73) Assignee: Snow Brand Milk Products Co., Ltd., Sapporo (JP)

( * ) Notice: Subject to any disclaimer, the term of this patent is extended or adjusted under 35 U.S.C. 154(b) by 0 days.

(21) Appl. No.: 09/297,960

(22) PCT Filed: Sep. 10, 1998

(86) PCT No.: PCT/JP98/04076
§ 371 Date: May 27, 1999
§ 102(e) Date: May 27, 1999

(87) PCT Pub. No.: WO99/13065
PCT Pub. Date: Mar. 18, 1999

(30) Foreign Application Priority Data

Sep. 10, 1997 (JP) .................................................... 9-262693
Jul. 14, 1998 (JP) ................................................... 10-214831

(51) Int. Cl.$^7$ .............................. C12Q 1/68; C12P 19/34; C07H 21/04

(52) U.S. Cl. ........................... 435/6; 435/91.2; 536/24.33
(58) Field of Search .................... 435/6, 91.2; 536/24.33

(56) References Cited

U.S. PATENT DOCUMENTS 5,849,488 * 12/1998 Alatossava et al. ...................... 435/6
6,143,560 * 11/2000 Imamura et al. ...................... 435/376

FOREIGN PATENT DOCUMENTS

94/28126 * 12/1994 (WO) .

OTHER PUBLICATIONS

Leroux et al., J. Biol. Chem. 267(9), 6147–6157 (1992).*
Lindquist et al., BioTechniques 17(4), 692–696 (1994).*

* cited by examiner

Primary Examiner—Kenneth R. Horlick
(74) Attorney, Agent, or Firm—Darby & Darby

(57) ABSTRACT

A novel primer is provided which is useful in the reverse transcription polymerase chain reaction to amplify $\alpha_{s1}$-casein gene and keratin gene contained in milk. A method is also provided for using the expression ratio of their genes to examine the pathological conditions of mammalian mastitis or determine the milk protein synthesis level in mammary gland cells. The method is quick and accurate and avoids the need for excising mammary gland tissue.

13 Claims, 1 Drawing Sheet

METHOD FOR DETERMINING MASTITIS USING KERATIN AND CASEIN WHICH ARE AMPLIFIED BY PRIMERS

FIELD OF THE INVENTION

This invention relates to primers capable of hybridization with keratin gene or $\alpha_{S1}$-casein gene. The primers of the present invention can be used for the test of mastitis of mammals such as cows and determination of synthetic level of milk protein in mammary gland cells.

BACKGROUND OF THE INVENTION

Mastitis is an inflammatory disease of mammary tissue caused by infiltrated pathogenic microorganisms in the breast, and causes great economic loss in dairy farming such as decreased milk quantity and selection and screening of infected cows. Fundamental countermeasures to mastitis include early diagnosis and treatment depending on the determination of increased number of somatic cells in milk and PL test in general. These determinations depend on the increased number of somatic cells and tendency to exhibit alkaline pH in milk due to the infection. However, these factors vary greatly between individuals and lactation period, and are deemed not always sufficient for early diagnosis of mastitis. Generally, mastitis milk shows the changes in components with a characteristically decreased content of casein, and a judgment of mastitis using the ratio of nitrogen content in casein and total nitrogen content in milk was tried, however, wide range of the determined values made the judgment unreliable.

On the other hand, the volume of milk or ratio of milk fat have been widely used as indicators to evaluation of milk production of a cow. However, the ratio of milk protein has recently become important in view of the improved production of milk products and/or the trend for better health. Among milk proteins especially casein is considered to be a reliable indicator for evaluation of milk quality. However, conventional method for determination was carried out by separation of casein from milk and measurement of nitrogen content in the separated casein fraction. The procedure is troublesome and requires long period of time without sufficient sensitivity for detailed investigation. Recently, simple determination method of casein content in milk with infrared or near infrared spectroscopy was developed, however, coordination with the observed results with those of conventional methods remain unsolved.

Changes of milk components result from various factors and one presumed mechanism is an infiltration of a causal pathogenic bacteria of mastitis in the mammary gland through lactiferous duct followed by adhesion to epithelial cells of mammary gland resulting the inhibition of biosynthesis of milk components. This means that determination of changes in the ability for production of milk components with mammary gland epithelial cells with some method will provide early detection and diagnosis of mastitis.

The inventors of the present invention aimed to use $\alpha_{S1}$-casein, a most typical protein among milk proteins synthesized in epithelial cells of mammary gland of cow, as an indicator for the level of milk protein synthesis.

Recently to detect the amount of transcription of mRNA a reverse transcription-polymerase chain reaction (RT-PCR) method using a polymerase chain reaction (PCR method: U.S. Pat. Nos. 4,683,195 and 4,683,202) has been developed. The method can be applied for a sensitive qualitative and quantitative determinations of an expressed protein in cells. However, extraction of RNA from biopsied mammary tissue of a cow for the diagnosis of mastitis is practically inapplicable for industrial cow animals and no method has been reported to extract RNA from mammary gland epithelial cells without invasion.

Extraction of RNA from milk demands minimum decomposition of RNA with a ribonuclease. In addition, the number of mammary gland epithelial cells is much smaller than those of other cells and to minimize the influence of milk component on RNA extraction, centrifugation of milk to precipitat cells prior to the extraction is indispensable.

Keratin gene is a cytoskeleton gene which specifically expresses only in epithelial cells including various subtypes and differently express in species and sites. Thus, the primer used for an indicator of the amount of bovine mammary gland epithelial cells requires hybridization with keratin gene which expresses in bovine mammary gland epithelial cells and a correlation between the expressed amount of keratin gene and number of epithelial cells is necessary. Furthermore, $\alpha_{S1}$-casein is known to have four genetic variations and a primer capable of hybridization with any one of a $\alpha_{S1}$-casein variants is required for universal detection method.

DISCLOSURE OF THE INVENTION

The inventors of the present invention have earnestly investigated a method for preparation of RNA from milk and an accurate detection method of mastitis using the resultant RNA under these circumstances, and found a method for preparation of RNA derived from mammary gland epithelial cells in milk by rapid cooling of milk to ice temperature, dilution with a buffer followed by centrifugation to give cellular pellets. The procedure may be repeatedly carried out, if necessary, and RNA is extracted from the resultant cellular pellets. A primer capable of partial amplification of the keratin gene designed to give size of 274 bp in consideration of the amplification range of reactivity in PCR was prepared using a basic (type 2) component 3 keratins. Also, a primer capable of partial amplification of the $\alpha_{S1}$-casein gene designed to give a size of 351 bp in consideration of the amplification range of reactivity in a conserved sequence of the genetic variants of $\alpha_{S1}$-casein gene was synthesized according to conventional methods, and a reverse transcription-polymerase chain reaction [RT-PCR; Wang et al., Proc. Natl. Acad. Sci., USA, 86, 9717–9721 (1989)] using these primers was performed to simply, quickly and accurately detect mastitis and accomplished the present invention.

Therefore, one object of the present invention is to provide a novel DNA for preparation of primers capable of hybridization with keratin gene and $\alpha_{S1}$-casein gene.

The other object of the present invention is to provide a process for amplification of keratin gene and/or casein gene using the primers.

Further object of the present invention is to provide a method for the test and diagnosis of mastitis using the process for amplification of keratin gene and/or casein gene, or a process for determination of synthetic level of milk protein with mammary gland cells. That is, the present invention relates to primers shown by SEQ ID NO: 1–4.

Further, the present invention relates to a primer which hybridizes with keratin gene expressed by SEQ ID NO: 1 or 2. In addition, the present invention relates to a primer which hybridizes with $\alpha_{S1}$-casein gene expressed by SEQ ID NO: 3 or 4.

Furthermore, the present invention relates to a process for amplification of keratin gene and/or casein gene contained in milk by a reverse transcription-polymerase chain reaction (RT-PCR) using these primers.

Said amplification of the present invention is carried out by rapid cooling of milk to temperature of ice, dilution with a buffer, centrifugation, extraction of RNA from the formed precipitates or pellets, followed by amplification of keratin gene and/or casein gene using the RNA as a template and the primers.

Furthermore, the present invention relates to a process for estimation of the ratio of expressed $\alpha_{S1}$-casein gene and keratin gene in milk using these gene amplification methods, and a method for the test of morbidity of mastitis or the level of productivity of milk protein with mammary gland cells.

As described above, the present invention relates to the primers shown in SEQ ID NO: 1–4 in the Sequence Listing. The primer hybridizes with keratin gene and has a sequence of CAG-TGT-CGG-GGG-CTC-TGG (SEQ ID NO: 1 or ATG-TGG-GTC-TGC-GAT-AGG-CT? (SEQ ID NO. ). Also, the primer hybridizes with $\alpha_{S1}$-casein gene and has sequence of GTC-AAG-TGA-ATT-CTG-AGG (SEQ ID NO: 3) or TGG-CAC-TTA-CAG-GAG-AAG SEQ ID NO: 4).

These oligonucleotides are designed in consideration of the degree of specificity, sizes, contents of GC, Tm values and so forth and can be prepared with conventional chemical synthetic methods. Their purity and yields can be confirmed with electrophoreses and determination of absorbencies.

The present invention is used for diagnosis of mastitis using these primers, particularly for the diagnosis of bovine mastitis. The milk to be tested by the present invention includes those of mammals without particular restriction and bovine milk is preferably tested.

The cellular RNA contained in the milk to be tested in the present invention is prepared as shown below. That is, milk is collected under hygienic condition as far as possible and rapidly cooled to temperature of ice. The cooled milk is diluted with a suitable buffer, preferably physiological phosphate buffer [PBS(−)], and centrifuged to collect precipitates. The procedure of dispersion in a buffer, preferably in PBS(−), and centrifugation may be repeated, if necessary. Cellular RNA contained in milk is extracted from the resultant precipitates with conventional methods. Furthermore, extraction of mRNA may be carried out, if necessary.

The resultant RNA is used as a template for the synthesis of complementary DNA (cDNA) with a reverse transcription reaction using a reverse transcriptase. In the synthesis, an oligo-dT-primer or a random primer, preferably the oligonucleotide shown by SEQ ID NO: 2 or 4 is used as an antisense primer. Then, the resultant cDNA is used as a template and an oligonucleotide shown by one of SEQ ID NO: 1 and No. 2 is used as a sense primer and an antisense primer respectively, and No. 3 and No. 4 as a sense primer and an antisense primer respectively, for PCR with a DNA polymerase. The PCR reaction mixture is separated with electrophoresis and stained with a suitable pigment, preferably an ethidium bromide solution. The intensity of stained bands is measured with a suitable image analyzer. The intensity of staining of band in PCR reaction solution using the oligonucleotide shown by SEQ ID NO: 1 and oligonucleotide shown by Seq. No. 2 as a sense primer and an anti-sense primer respectively, shows the amount of expression of keratin gene of basic (type 2) component type 3. The intensity of staining of band in PCR reaction solution using the oligonucleotide shown by SEQ ID NO: 3 and No. 4 as a sense primer and an anti-sense primer respectively, shows the amount of expression of $\alpha_{S1}$-casein. The ratio of expressed amounts of $\alpha_{S1}$-casein gene and keratin gene reveals the amount of expression of $\alpha_{S1}$-casein gene of mammary epithelial cells in breast to be tested. The ratio of 1.0 or over represents normal, the ratio of 0.5 or over and less than 1.0, slight mastitis, and the ratio of less than 0.5 severe mastitis. Also, the ratio of expressed amounts of keratin gene and $\alpha_{S1}$-casein gene obtained by the method shown above from the amount of expressed $\alpha_{S1}$-casein gene and the amount of keratin gene gives the expressed amount of $\alpha_{S1}$-casein gene in mammary epithelial cells in breast to be tested. The values are compared in different cows and feeding conditions to give a standard for the evaluation of milk quality such as ability in casein synthesis or a standard for evaluation of feed.

The determination methods shown above are summarized by the below mentioned flow chart.

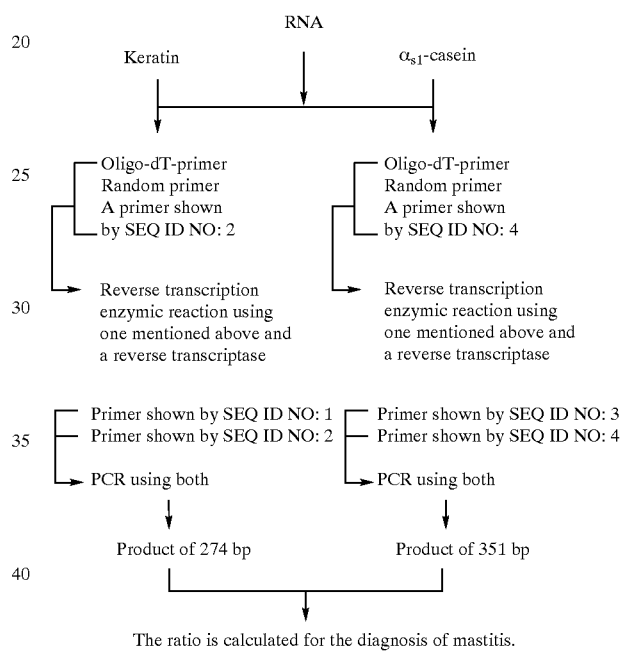

BEST MODE FOR CARRYING OUT THE INVENTION

The present invention will be explained in detail by the following examples. However, these examples are enumerated as mere references without any restriction of the scope of the present invention.

EXAMPLE 1

Preparation of RNA From Milk

Figure 1:
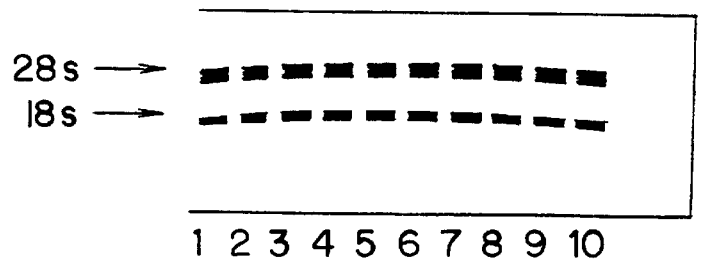
FIG. 1 shows an electrophoretic diagram of RNA extracted from milk in Example 1. In the FIG., lanes 1–10 show sample Nos. of cows, and 18s and 28s represent ribosome RNA, respectively.

Milk of 10 cows shown in Table 1 was drawn 50 ml each in sterilized vessels, rapidly cooled on ice and transported to laboratories under cooling. The milk was diluted to 2-fold volume with PBS(−), centrifuged at 4° C. and 1,500 G for 5 min. to collect precipitates. The collected precipitates were dispersed in 50 ml of PBS(−), centrifuged under the same conditions to recover precipitates. The precipitates were treated with RNAzol (TelTest) to extract sample RNA. The extracted sample RNA was subjected to SDS-polyacrylamide gel electrophoresis (SDS-PAGE), and the absorbance at 260 and 280 nm were determined and their ratio was estimated. The electrophoretic diagram is shown in FIG. 1 and the ratios of absorbance are shown in Table 1, respectively. The amount of RNA and impurities (protein, etc.) were measured with absorbance at 260 and 280 nm, respectively, and the purity was estimated from the ratio of absorbencies at 260 nm/280 nm. The ratio of absorbance was 2.0 for pure sample. Samples with the ratio in a range of 1.9–2.1 are judged as highly pure and can be used for RT-PCR.

The results showed that the samples are pure enough for RT-PCR.

TABLE 1

| Sample | Absorbance | | |
|---|---|---|---|
| No. | 260 nm | 280 nm | Ratio |
| 1 | 0.746 | 0.363 | 2.055 |
| 2 | 0.890 | 0.441 | 2.018 |
| 3 | 0.733 | 0.385 | 1.904 |
| 4 | 0.534 | 0.280 | 1.907 |
| 5 | 0.894 | 0.447 | 2.000 |
| 6 | 0.384 | 0.196 | 1.959 |
| 7 | 0.681 | 0.358 | 1.902 |
| 8 | 0.856 | 0.441 | 1.941 |
| 9 | 0.894 | 0.466 | 1.918 |
| 10 | 0.851 | 0.438 | 1.943 |

EXAMPLE 2

A Method for Diagnosis of Bovine Mastitis Using the Primer and the Results

Figure 2:
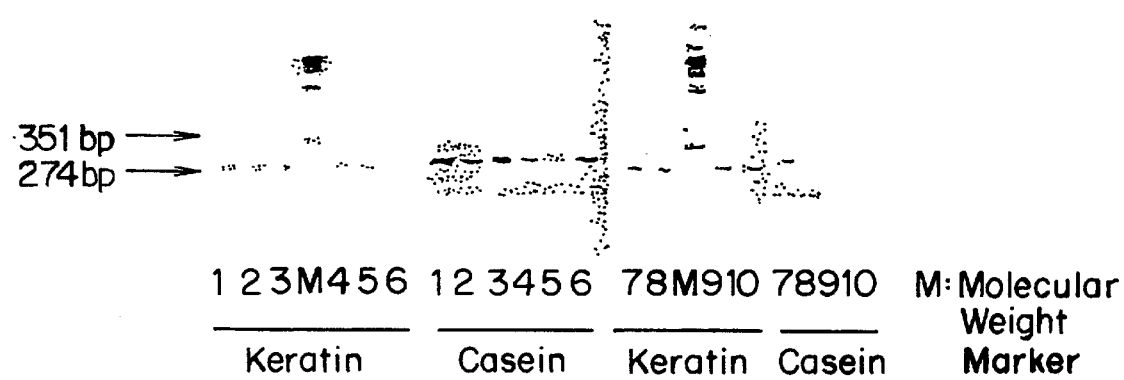
FIG. 2 shows an electrophoretic diagram of $\alpha_{S1}$-casein and keratin in sample of Example 2. In the FIG., lanes 1–10 show sample Nos. of cows, M represents molecular weight, and 274 bp and 351 bp represent the aimed band, respectively.

The RNAs of cow obtained in Example 1 was divided in two micro-test tubes to contain 1 μg each as total RNA. Primary stranded cDNA was synthesized with a reverse transcriptase (Gibco) in test tubes each containing the primer of SEQ ID NO: 2 or SEQ ID NO: 4, respectively. The reaction mixture was divided 1 μl each in micro-test tubes and subjected to PCR with conventional method using AmpliTaqDNA polymerase (Perkin-Elmer Japan Co., Ltd.). The reaction condition for PCR was 96° C. for denaturation for 1 min., annealing at 56° C. for 1 min., and chain elongation reaction at 72° C. for 1 min. The amplified PCR products were separated with 2% agarose gel electrophoresis and visualized by staining with ethidium bromide. The stained images of product were scanned with a scanner (Hewlett-Packard Co.) and taken up in a computer (Apple Computer Inc.). The intensity of aimed stained band of keratin gene in the sample at 274 bp and that of $\alpha_{S1}$-casein gene in the sample at 351 bp were numerically analyzed with an image analyzing program (NIHImage). The stained band is shown in FIG. 2 and the intensity of stained image for each component and the ratio of stained intensity of band of $\alpha_{S1}$-casein to that of keratin are shown in Table 3. The results of diagnosis judged from the ratio of intensity of stained image of $\alpha_{S1}$-casein to that of keratin agreed with those judged from macroscopic observation and number of somatic cells. Thus, the method of the present invention is confirmed to be effective as a test method of mastitis.

TABLE 2

| Sample No. | Diagnosis |
|---|---|
| 1 | Normal |
| 2 | Normal |
| 3 | Normal |
| 4 | Chronic mastitis |
| 5 | Chronic mastitis |
| 6 | Chronic mastitis |
| 7 | Chronic mastitis |
| 8 | Clinical mastitis |
| 9 | Clinical mastitis |
| 10 | Clinical mastitis |

TABLE 3

| Sample No. | Intensity of band (average of pixel) | | Ratio | Diagnosis |
|---|---|---|---|---|
| | $\alpha_{S1}$-casein | keratin | | |
| 1 | 62.54 | 54.56 | 1.15 | Normal |
| 2 | 42.38 | 41.99 | 1.01 | Normal |
| 3 | 47.42 | 27.45 | 1.73 | Normal |
| 4 | 13.43 | 15.70 | 0.86 | Slight |
| 5 | 9.20 | 10.44 | 0.88 | Slight |
| 6 | 10.60 | 10.67 | 0.99 | Slight |
| 7 | 21.13 | 30.51 | 0.69 | Slight |
| 8 | 14.56 | 30.84 | 0.47 | Severe |
| 9 | 6.63 | 31.00 | 0.21 | Severe |
| 10 | 4.37 | 30.57 | 0.14 | Severe |

INDUSTRIAL APPLICABILITY

A novel primer capable of hybridization with keratin gene and a novel capable of hybridization with $\alpha_{S1}$-casein gene, and a process for amplification of keratin gene and/or casein gene contained in milk with RT-PCR these primers are provided by the present invention. Furthermore, a for the test of mastitis and a method for determination of the level for synthesis of milk protein in mammary gland cells are provided. The present invention is useful for a simple, rapid and highly accurate test method of mastitis, particularly bovine mastitis without resection of mammary gland tissue, and a determination method for the level of milk protein synthesis in mammary gland cells.

What is claimed is:

1. A method for early detection and diagnosis of mastitis in mammals which comprises the steps of:
   1) amplifying keratin gene and casein gene contained in the milk of such mammals by a reverse transcription-polymerase chain reaction,
   2) calculating the ratio of the expressed amount of casein gene to that of keratin gene, and
   3) evaluating the symptoms of the onset of mastitis by comparing the ratio with known ratios which have been determined to be indicative of mastitis.

2. A method for determination of the milk protein synthetic level of mammary gland cells which comprises the steps of:
   1) amplifying keratin gene and casein gene contained in said mammary gland cells,
   2) calculating the ratio of expressed amounts of casein gene to that of keratin gene, and
   3) evaluating the milk protein synthetic level of mammary gland cells by comparison with known ratios.

3. A method for the early detection and diagnosis of mastitis in mammals which utilizes the amplification of keratin gene and casein gene contained in the milk of such mammals by a reverse transcription-polymerase chain reaction (RT-PCR) using at least one primer of SEQ ID NO: 1 or 2, and at least one primer of SEQ ID NO: 3 or 4, which method comprises the steps of:
   a) rapidly cooling the milk,
   b) extracting RNA from said milk,
   c) amplifying the keratin gene and casein gene using the RNA as a template and the primers, and
   d) calculating the ratio of the expressed amount of casein gene to that of keratin gene, and evaluating the symptoms of onset of mastitis by comparing the ratio with known ratios which have been determined to be indicative of mastitis.

4. A method for the early detection and diagnosis of mastitis in mammals which utilizes the amplification of keratin gene and casein gene contained in the milk of such mammals by a reverse transcription-polymerase chain reaction (RT-PCR) using at least one primer of SEQ ID NO: 1 or 2, and at least one primer of SEQ ID NO: 3 or 4, which method comprises the steps of:

a) rapidly cooling the milk.

b) diluting the milk with a buffer solution, c) centrifuging the diluted milk solution to form precipitates, d) extracting RNA from said precipitates, e) amplifying the keratin gene and casein gene using the RNA as a template and the primers, and f) calculating the ratio of the expressed amount of casein gene to that of keratin gene, and evaluating the symptoms of onset of mastitis by comparing the ratio with known ratios which have been determined to be indicative of mastitis.

5. The method of claim 4 wherein steps (b) and (c) are repeated before step (d).

6. The method of claim 4 wherein in step (a) the milk is cooled to the approximate temperature of ice.

7. The method of claim 4 wherein in step (b) the buffer solution is PBS(−).

8. The method of claim 4 wherein the RNA is extracted with RNAzol.

9. The method of claim 4 wherein the primers used are SEQ ID NO: 1 and SEQ ID NO: 3.

10. The method of claim 4 wherein the primers used are SEQ ID NO: 2 and SEQ ID NO: 4.

11. The method of claim 4 wherein the primers used are a combination of SEQ ID NO: 1 and NO: 2, and a combination of SEQ ID NO: 3 and NO: 4.

12. A primer pair capable of hybridization with keratin gene consisting of SEQ ID NO: 1 and SEQ ID NO: 2.

13. A primer pair capable of hybridization with casein gene consisting of SEQ ID NO: 3 and SEQ ID NO: 4.

\* \* \* \* \*

SEQUENCE LISTING (1) GENERAL INFORMATION:

(iii) NUMBER OF SEQUENCES: 4

(2) INFORMATION FOR SEQ ID NO:1:

-continued

```
    (i) SEQUENCE CHARACTERISTICS:
        (A) LENGTH: 18
        (B) TYPE: Nucleic Acid
        (C) STRANDEDNESS: Single
        (D) TOPOLOGY: Linear (xi) SEQUENCE DESCRIPTION: SEQ ID NO:1:

GAGTGTCGGG GGCTCTGG                                                    18

(2) INFORMATION FOR SEQ ID NO:2:

(i) SEQUENCE CHARACTERISTICS:
        (A) LENGTH: 20
        (B) TYPE: Nucleic Acid
        (C) STRANDEDNESS: Single
        (D) TOPOLOGY: Linear (ix) SEQUENCE DESCRIPTION: SEQ ID NO:2:

ATGTGGGTCT GCGATAGGCT                                                  20

(2) INFORMATION FOR SEQ ID NO:3:

(i) SEQUENCE CHARACTERISTICS:
        (A) LENGTH: 18
        (B) TYPE: Nucleic Acid
        (C) STRANDEDNESS: Single
        (D) TOPOLOGY: Linear (ii) MOLECULE TYPE: Peptide (ix) SEQUENCE DESCRIPTION: SEQ ID NO:3:

GTCAAGTGAA TTCTGAGG                                                    18

(2) INFORMATION FOR SEQ ID NO:4:

(i) SEQUENCE CHARACTERISTICS:
        (A) LENGTH: 18
        (B) TYPE: Nucleic Acid
        (C) STRANDEDNESS: Single
        (D) TOPOLOGY: Linear (xi) SEQUENCE DESCRIPTION: SEQ ID NO:4:

TGGCACTTAC AGGAGAAG                                                    18
```